United States Patent
Matkovich

[11] Patent Number: 5,868,433
[45] Date of Patent: ***Feb. 9, 1999

[54] CONNECTOR ASSEMBLY

[75] Inventor: Vlado I. Matkovich, Glen Cove, N.Y.

[73] Assignee: Pall Corporation, Glen Cove, N.Y.

[ * ] Notice: The term of this patent shall not extend beyond the expiration date of Pat. No. 5,399,101.

[21] Appl. No.: 608,216

[22] Filed: Feb. 28, 1996

Related U.S. Application Data

[63] Continuation of Ser. No. 369,091, Jan. 5, 1995, abandoned, which is a continuation of Ser. No. 956,854, Oct. 2, 1992, Pat. No. 5,393,101.

[51] Int. Cl.⁶ .............................. A61M 5/00; F16L 47/00; F16L 55/00
[52] U.S. Cl. .............................. 285/3; 604/192; 604/198; 604/905; 285/915; 285/319
[58] Field of Search ................ 285/3, 319, 915; 604/905, 411, 192, 198, 283, 145, 110, 408, 412–415

[56] References Cited

U.S. PATENT DOCUMENTS

| | | |
|---|---|---|
| 3,784,235 | 1/1974 | Kessler et al. . |
| 3,890,971 | 6/1975 | Leeson et al. . |
| 3,902,489 | 9/1975 | Carter . |
| 3,968,195 | 7/1976 | Bishop . |
| 3,986,508 | 10/1976 | Barrington . |
| 4,019,512 | 4/1977 | Tenczar . |
| 4,022,205 | 5/1977 | Tenczar . |
| 4,022,496 | 5/1977 | Crissy et al. . |
| 4,030,494 | 6/1977 | Tenczar . |
| 4,161,949 | 7/1979 | Thanawalla . |
| 4,191,225 | 3/1980 | Ogle . |
| 4,201,208 | 5/1980 | Cambio, Jr. . |
| 4,256,106 | 3/1981 | Shoor . |
| 4,265,280 | 5/1981 | Ammann et al. . |
| 4,289,337 | 9/1981 | Roe . |
| 4,334,551 | 6/1982 | Pfister . |
| 4,336,802 | 6/1982 | Stone et al. ............... 604/415 |
| 4,368,729 | 1/1983 | Dossin ..................... 604/415 |
| 4,410,321 | 10/1983 | Pearson et al. . |
| 4,418,945 | 12/1983 | Kellogg . |
| 4,443,215 | 4/1984 | Smith . |
| 4,457,749 | 7/1984 | Bellotti et al. . |
| 4,488,961 | 12/1984 | Spencer . |
| 4,507,119 | 3/1985 | Spencer . |
| 4,511,359 | 4/1985 | Vaillancourt . |
| 4,516,971 | 5/1985 | Spencer . |
| 4,521,263 | 6/1985 | Benin et al. . |
| 4,531,768 | 7/1985 | Summers . |
| 4,564,054 | 1/1986 | Gustavsson . |

(List continued on next page.)

FOREIGN PATENT DOCUMENTS

| | | |
|---|---|---|
| 0256640 | of 1987 | European Pat. Off. . |
| 0545598 | 6/1993 | European Pat. Off. . |
| 1322012 | 5/1962 | France . |
| 1380396 | 1/1964 | France . |
| 2097975 | 2/1972 | France . |
| 2608250 | 12/1986 | France . |
| 2606643 | 5/1988 | France . |
| 2614386 | 10/1988 | France . |
| 1929522 | 6/1969 | Germany . |
| 677964 | 1/1989 | Switzerland . |
| 1132443 | 11/1965 | United Kingdom . |
| 2008705 | 6/1979 | United Kingdom . |
| WO 83/03538 | 10/1983 | WIPO . |
| WO 89/00432 | 1/1989 | WIPO . |
| WO 92/19314 | 11/1992 | WIPO . |
| WO 94/08173 | 4/1994 | WIPO . |

*Primary Examiner*—Eric K. Nicholson
*Attorney, Agent, or Firm*—Leydig, Voit & Mayer

[57] ABSTRACT

A connector assembly includes a first fitting defining a first aperture, and a second fitting couplable to the first fitting and defining a second aperture. In some embodiments, each of the first and second fittings includes a sealing layer sealing its aperture. In other embodiments, each of the first and second fittings includes a removable layer overlying its aperture. The connector assembly may include a stem member which is mounted in the first fitting and includes a head axially movable into the aperture of the second fitting.

66 Claims, 6 Drawing Sheets

U.S. PATENT DOCUMENTS

| | | |
|---|---|---|
| 4,573,978 | 3/1986 | Reilly . |
| 4,610,469 | 9/1986 | Wolff-Mooij . |
| 4,610,670 | 9/1986 | Spencer . |
| 4,617,012 | 10/1986 | Vaillancourt . |
| 4,619,642 | 10/1986 | Spencer . |
| 4,636,204 | 1/1987 | Christopherson et al. . |
| 4,680,025 | 7/1987 | Kruger et al. . |
| 4,737,214 | 4/1988 | Leurink et al. . |
| 4,753,697 | 6/1988 | Shaposka et al. . |
| 4,767,400 | 8/1988 | Miller et al. . |
| 4,770,735 | 9/1988 | Shaposka et al. . |
| 4,792,163 | 12/1988 | Kulle . |
| 4,793,880 | 12/1988 | Shaposka et al. . |
| 4,816,221 | 3/1989 | Harvey et al. . |
| 4,828,557 | 5/1989 | Persidosky . |
| 4,832,773 | 5/1989 | Shaposka et al. . |
| 4,838,875 | 6/1989 | Somor ................................. 604/408 |
| 4,840,690 | 6/1989 | Melinyshyn et al. . |
| 4,843,017 | 6/1989 | Oberhardt et al. . |
| 4,864,101 | 9/1989 | Shaposka et al. . |
| 4,897,138 | 1/1990 | Shaposka et al. . |
| 4,913,756 | 4/1990 | Shaposka et al. . |
| 4,933,036 | 6/1990 | Shaposka et al. . |
| 4,941,517 | 7/1990 | Galloway . |
| 4,944,728 | 7/1990 | Carrell et al. . |
| 4,950,260 | 8/1990 | Bonaldo . |
| 4,978,446 | 12/1990 | Lobdell .................... 604/408 |
| 4,995,869 | 2/1991 | McCarthy . |
| 4,998,713 | 3/1991 | Vaillancourt . |
| 4,998,921 | 3/1991 | Vickroy et al. . |
| 4,998,927 | 3/1991 | Vaillancourt . |
| 5,017,259 | 5/1991 | Kohsai . |
| 5,065,783 | 11/1991 | Ogle, II . |
| 5,067,950 | 11/1991 | Broadnax, Jr. . |
| 5,117,875 | 6/1992 | Marrucchi . |
| 5,122,123 | 6/1992 | Vaillancourt ........................ 604/192 |
| 5,122,129 | 6/1992 | Olson et al. . |
| 5,158,549 | 10/1992 | McCarthy . |
| 5,195,993 | 3/1993 | Gianakos . |
| 5,224,936 | 7/1993 | Gallagher . |
| 5,232,454 | 8/1993 | Hollister . |
| 5,250,030 | 10/1993 | Corsich . |
| 5,267,972 | 12/1993 | Anderson . |
| 5,279,591 | 1/1994 | Simon . |
| 5,295,972 | 3/1994 | Mischenko . |
| 5,380,049 | 1/1995 | Smowton . |
| 5,393,101 | 2/1995 | Matkovich . |
| 5,437,639 | 8/1995 | Malenchek . |
| 5,492,147 | 2/1996 | Challender et al. .................. 604/905 |
| 5,688,254 | 11/1997 | Lopez et al. ......................... 604/905 |

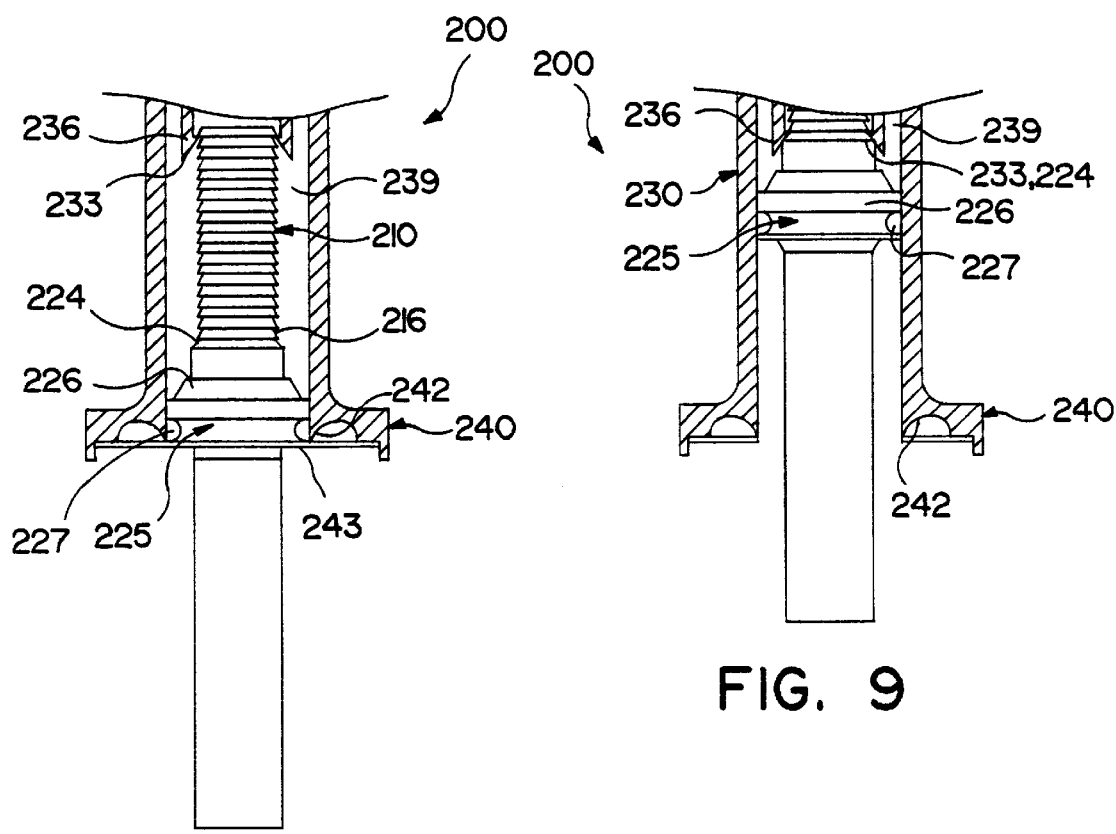
FIG. 8
FIG. 9
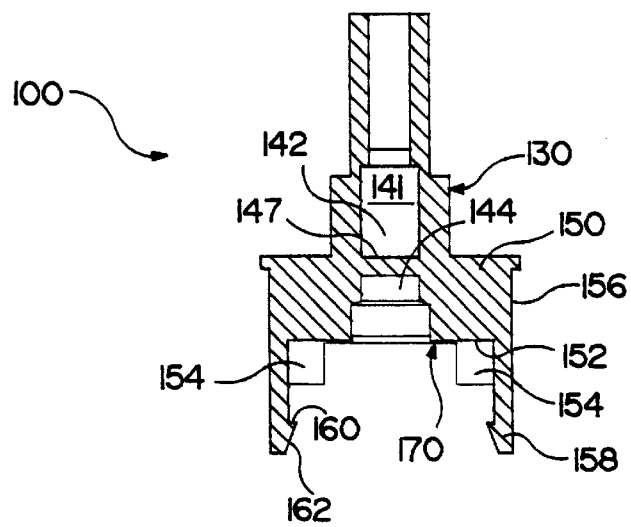
FIG. 10

CONNECTOR ASSEMBLY

This disclosure is a continuation of patent application Ser. No. 08/369,091, filed Jan. 5, 1995 and abandoned in favor of the present disclosure, which is a continuation of Ser. No. 956,854, now U.S. Pat. No. 5,393,101, filed Oct. 2, 1992.

FIELD OF THE INVENTION

The present invention relates to a connector assembly. More particularly, the invention relates to a connector assembly which maintains the sterility of a fluid, for example, a biological fluid, which passes through the connector assembly.

BACKGROUND OF THE INVENTION

Connector assemblies have been developed to handle fluids, e.g., biological fluids, while preserving their condition. More particularly, connectors have been developed to preserve the condition of a fluid, or maintain a fluid free of contaminants. Freedom from contaminants refers to a relative amount of contaminants and is variously defined according to a specific industry, fluid and/or intended use. For example, a biological fluid which is substantially free of contaminants is considered free of viable micro-organisms, and is typically referred to as "sterile". Connector assemblies for use with biological fluids, for example, have been fashioned to preserve sterility of the fluid.

Attempts have been made to develop connector assemblies which isolate a fluid from the ambient environment of the connector, and from contaminants entrained in the ambient. Such connectors typically define a fluid conduit which is isolated from the ambient. Some conventional connector assemblies include mating male and female connectors having opposing, exposed surfaces. One surface may comprise the surface of a membrane, for example, while the other surface may comprise the surface of a rubber septum forming a blind end of an elastic, collapsible tube. These surfaces may be wiped with an antiseptic, then resiliently urged in contact when the connectors are coupled. Other conventional connector assemblies provide a removable protective cover on each opposing surface to be contacted. These covers must be removed prior to actually coupling the connectors.

Many problems are associated with these conventional connector assemblies. For example, wiping the surfaces with an antiseptic or removing the covers of these conventional connector assemblies may not sufficiently protect the fluid flowing through these assemblies. The surfaces are wiped and the covers are removed usually by hand. Although the attendant may use surgical gloves, a gloved finger may trail the antiseptic wipe along the protected surface, depositing on the surface contaminants that were on the glove. To unfasten and remove a cover, the gloved hand must manipulate the removable cover in intimate proximity to the protected surface under the cover, again risking incidental contact and the transmission of contaminants between the glove and the protected surface.

In addition, once the surfaces are wiped with an antiseptic or the protective covers are removed from the protected surfaces, the surfaces are exposed to the contaminant-laden ambient environment. For example, as the connectors are brought together, dust, micro-organisms, and other airborne contaminants may contact the protected surfaces, even if the connectors are quickly mated. Thus, while these conventional connector assemblies have been developed to form a sterile connection, none adequately protect the fluid flowing through the connector assembly.

SUMMARY OF THE INVENTION

In accordance with one aspect of the invention, a connector assembly comprises a first fitting defining a first aperture, a second fitting defining a second aperture, a first membrane assembly sealing the first aperture, a second membrane assembly sealing the second aperture, and an axially resilient seat disposed between the first and second fittings. The axially resilient seat urges the first and second fittings into biased opposition to maintain the first and second membrane assemblies in positive contact. The axially resilient seat includes a first section comprising a substantially cylindrical hub and a resilient connector. The cylindrical hub has a first diameter and defines a rim upon which the first membrane assembly is disposed. The resilient connector connects the first section to the first fitting and provides an axially resilient connection between the first section and the first fitting. The resilient connector includes a neck having a second diameter less than the first diameter. The resilient seat and the first fitting comprise a single, integral molded structure formed from a polymeric material.

In accordance with another aspect of the invention, a connector assembly comprises a first fitting defining a first aperture, a second fitting defining a second aperture, a first removable contamination containment layer overlying the first aperture, a second removable contamination containment layer overlying the second aperture, and an axially resilient seat disposed between the first and second fittings. The first and second fittings are couplable to provide positive contact between the first and second removable contamination containment layers. The axially resilient seat includes a substantially cylindrical hub having a first diameter and a neck having a second diameter less than the first diameter. The hub defines a rim, and the first contamination containment layer removably contacts the rim of the hub.

In accordance with still another aspect of the invention, a connector assembly comprises a first fitting defining a first aperture, a second fitting defining a second aperture, a first removable contamination containment layer overlying the first aperture, a second removable contamination containment layer overlying the second aperture, and an axially resilient seat disposed between the first and second fittings. The first and second fittings are couplable to provide positive contact between the first and second removable contamination containment layers. The axially resilient seat includes a substantially cylindrical hub and a neck, and at least one of the hub and neck is axially compressible. The hub defines a rim, and the first contamination containment layer removably contacts the rim.

In accordance with yet another aspect of the invention, a connector assembly comprises a first fitting, a second fitting, a resilient coupling mechanism, an interlock mechanism, and a stem member. The first fitting defines a first aperture and includes a first removable contamination containment layer overlying the first aperture. The second fitting defines a second aperture and includes a second removable contamination containment layer overlying the second aperture. The resilient coupling mechanism is positioned between the first and second fittings at the first and second apertures. The interlock mechanism includes at least one tongue. The tongue extends between the first and second fittings and is adapted to engage a corresponding surface to interlock the first and second fittings. The first and second fittings are couplable to provide positive contact between the first and second contamination containment layers. The stem member is mounted in the first fitting and includes a head axially movable through the first fitting into the aperture of the second fitting.

In accordance with yet still another aspect of the invention, a connector assembly comprises a first fitting, a second fitting, a resilient coupling mechanism, an interlock mechanism, and a piercing member. The first fitting defines a first aperture and includes a first removable contamination containment layer overlying the first aperture. The second fitting defines a second aperture and includes a second removable contamination containment layer overlying the second aperture. The resilient coupling mechanism is positioned between the first and second fittings at the first and second apertures. The interlock mechanism includes at least one tongue. The tongue extends between the first and second fittings and is adapted to engage a corresponding surface to interlock the first and second fittings. The first and second fittings are couplable to provide positive contact between the first and second contamination containment layers. The piercing member is mounted in the first fitting and is axially movable through the first fitting, through the sealing layers into the aperture of the second fitting In accordance with a further aspect of the invention, a connector assembly comprises a first fitting, a second fitting coupled to the first fitting, a stem member, and a breakable or severable element. The first fitting defines a first aperture and includes a first removable contamination containment layer overlying the first aperture. The second fitting defines a second aperture and includes a second removable contamination containment layer overlying the second aperture. The stem member is mounted in the first fitting and includes a head axially movable into the aperture of the second fitting. The breakable or severable element is positioned between the first fitting and the stem member and provides resistance to axial movement of the stem member into the second fitting.

In accordance with a still further aspect of the invention, a connector assembly comprises a first fitting, a second fitting, an interlock mechanism, a stem member, and an axial restraint. The first fitting defines a first aperture and includes a first removable contamination containment layer overlying the first aperture. The second fitting defines a second aperture and includes a second removable contamination containment layer overlying the second aperture. The interlock mechanism includes at least one tongue. The tongue extends between the first and second fittings and is adapted to engage a corresponding surface to interlock the first and second fittings. The first and second fittings are couplable to provide positive contact between the first and second contamination containment layers. The stem member is mounted in the first fitting and includes a head axially movable through the first fitting into the aperture of the second fitting. The axial restraint is coupled to the stem member to resist retraction of the stem member from the second fitting.

In accordance with yet further aspect of the invention, a connector assembly comprises a first fitting, a second fitting, an interlock mechanism, a piercing member, and an axial restraint. The first fitting defines a first aperture and includes a first removable contamination containment layer overlying the first aperture. The second fitting defines a second aperture and includes a second removable contamination containment layer overlying the second aperture. The interlock mechanism includes at least one tongue. The tongue extends between the first and second fittings and is adapted to engage a corresponding surface to interlock the first and second fittings. The first and second fittings are couplable to provide positive contact between the first and second contamination containment layers. The piercing member is mounted in the first fitting and axially movable through the sealing layers into the aperture of the second fitting. The axial restraint is coupled to the piercing member to resist retraction of the piercing member from the second fitting.

In accordance with yet still further aspect of the invention, a connector assembly comprises a first fitting, a second fitting coupled to the first fitting, a stem member, and a ratchet mechanism. The first fitting defines a first aperture and includes a first removable contamination containment layer overlying the first aperture. The second fitting defines a second aperture and includes a second removable contamination containment layer overlying the second aperture. The stem member is mounted in the first fitting and includes a head axially movable through the first fitting into the aperture of the second fitting. The ratchet mechanism is mounted to the stem member to lock the stem member within the second aperture of the second fitting.

The novel features and characteristics of this invention are set forth with particularity in the appended claims. However, the invention may best be understood with reference to the drawings, described below, and the accompanying detailed description of preferred embodiments.

BRIEF DESCRIPTION OF THE DRAWINGS

FIG. 8 is an elevation view in partial section of a male connector in another embodiment of a connector assembly according to the invention.

FIG. 9 is an elevation view in partial section of the male connector of FIG. 8, in final assembly.

FIG. 10 is an elevation view in section of another embodiment of a female connector in a connector assembly according to the invention.

DETAILED DESCRIPTION OF THE INVENTION

A connector assembly according to the present invention includes mating connectors or fittings which can be coupled to connect different fluid conduit sections, defining a fluid flow path. The connector assembly isolates the fluid flow path from the ambient environment and from contaminants present in the ambient environment and is preferably sterile. Consequently, a connector assembly according to the present invention is suitable for use in an open system, a closed system, or a closed sterile system.

Figure 1:
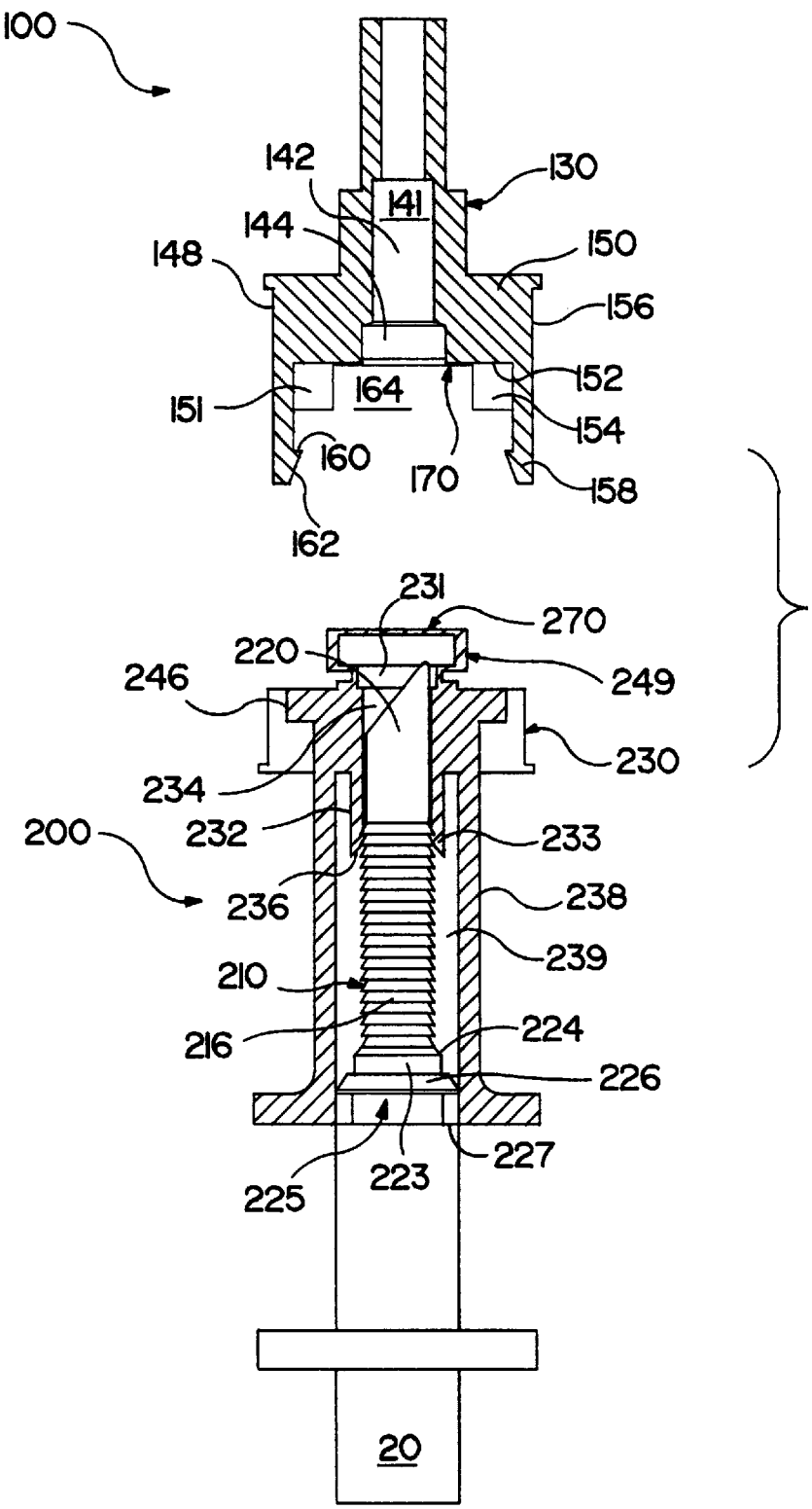
FIG. 1 is an elevation view, in partial section, of disassembled components of a connector assembly in one embodiment according to the invention.
Figure 2:
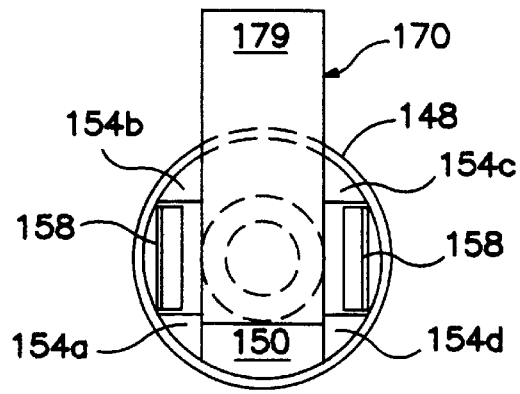
FIG. 2 is plan view of a female connector in the embodiment of FIG. 1.
Figure 3:
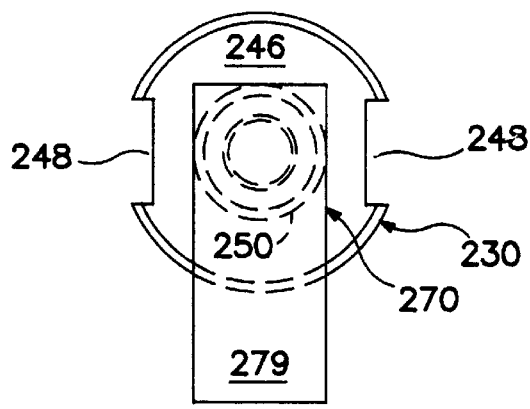
FIG. 3 is plan view of a male connector in the embodiment of FIG. 1.

In a preferred embodiment illustrated in FIGS. 1–3, the connector assembly comprises two connectors, preferably a female connector 100 and a male connector 200. Each connector may be attached to any suitable fluid conduit section, for example, an inlet or outlet of a housing such as a blood filter. In the illustrated embodiment, the fluid conduits comprise sections of tubing 10, 20. Each connector may comprise any structure suitable to conduct fluid communication, e.g. a housing of any form capable of containing fluid. The exemplary.female connector 100 generally comprises a fitting 130 and a membrane assembly 170. The exemplary male connector 200 generally comprises a stem 210, a fitting 230 and a membrane assembly 270.

In the disassembled view of FIG. 1, the connectors are disposed generally opposing each other. For directional orientation in the following discussion, each connector has a proximate end, nearest the opposing connector, and a distal end, furthest from the opposing connector. Also, since the exemplary connectors 100, 200 in FIG. 1 comprise generally elongated bodies, the term axial denotes disposition along their axes.

The female And male connectors may comprise a detent mechanism adapted to interlock the female connector in predetermined relation with the male connector. Thus, the female fitting 130 may include a bracket 148. The bracket 148 may be variously configured. The bracket 148 may comprise a socket or cup having any suitable plan form, e.g. rectangular or circular. In the illustrated embodiment, the bracket 148 comprises a U-shaped bracket or clevis. The representative bracket 148 is defined by a flange 150 and side walls 156. The flange 150 may assume a radially extending annular plan form, for example, as best seen in FIG. 2.

The side walls 156 depend away from the flange 150 and toward the opposing male connector 200. Tongues 158 may depend from the walls 156. The tongues 158 can be formed integrally with the walls 156, for example, by continuing middle sections of the walls 156. The tongues 158 can thus register in grooves 248 formed in a flange 246 of the male connector 200, best seen in FIG. 6. Accordingly, tongues 158 can be adapted to couple the female and male connectors 100, 200 in a tongue-in-groove engagement, as seen in the elevation view of FIG. 6 (in partial assembly). Tapers 162 can be formed at the proximate ends of the tongues 158 to guide the insertion of the tongues 158 into the grooves 248. Catches 160 can be formed which pass through the grooves 248, abutting a distal surface of the flange 246 and antagonistically locking the female and male connectors 100, 200, as will be detailed below.

A socket 164, adapted to receive the male connector 200, is defined by the space enclosed by the flange 150 and side walls 156. The proximate surface of the flange 150 (i.e. the flange surface closest the opposing male connector) provides a socket seat 152. The seat 152 serves as an abutment to the male connector 200 when the latter is positively engaged with the female connector 100.

The female fitting 130 may define an internal chamber or aperture 141 which may have any suitable configuration. The illustrated chamber 141 may comprise a bore 142 relieved at its proximate end into a counterbore 144. The flange sear 152 surrounds the counterbore 144. The illustrative female fitting 130 may be connected integrally with the section of tubing 10. The internal chamber 141 may be connected in fluid communication with the tubing 10.

In an important aspect of the invention, the female connector is adapted to contain fluid communication and preferably defines an isolated portion of the fluid path.

Accordingly, the chamber 141 is enclosed by a membrane assembly 170. The assembly of the female and male connectors 100, 200 may be surrounded by an atmosphere or ambient environment having contaminants. In one key function, the membrane assembly 170 isolates the chamber 141, and fluid therein, from the surrounding ambient and from contaminants present in the ambient.. Regardless of when or how the connector 100 is sterilized, the seal provided by the membrane assembly 170 is preferably secure enough to maintain the sterility within the chamber 141 of female connector 100.

The membrane assembly is preferably secured to the seat 152 of the female connector 100. Alternatively, the membrane assembly may be positioned in any other suitable location, such as within the internal chamber and sealed to the walls of the bore or the counterbore. The membrane assembly 170 can be secured to the seat 152 or the walls of the chamber 141 by a variety of means. Preferably, the membrane assembly 170 can be secured by ultrasonic welding. Alternatively, the membrane assembly 170 may be secured by a heat seal or bonded by an adhesive or a solvent, preferably along the periphery.

Figure 6:
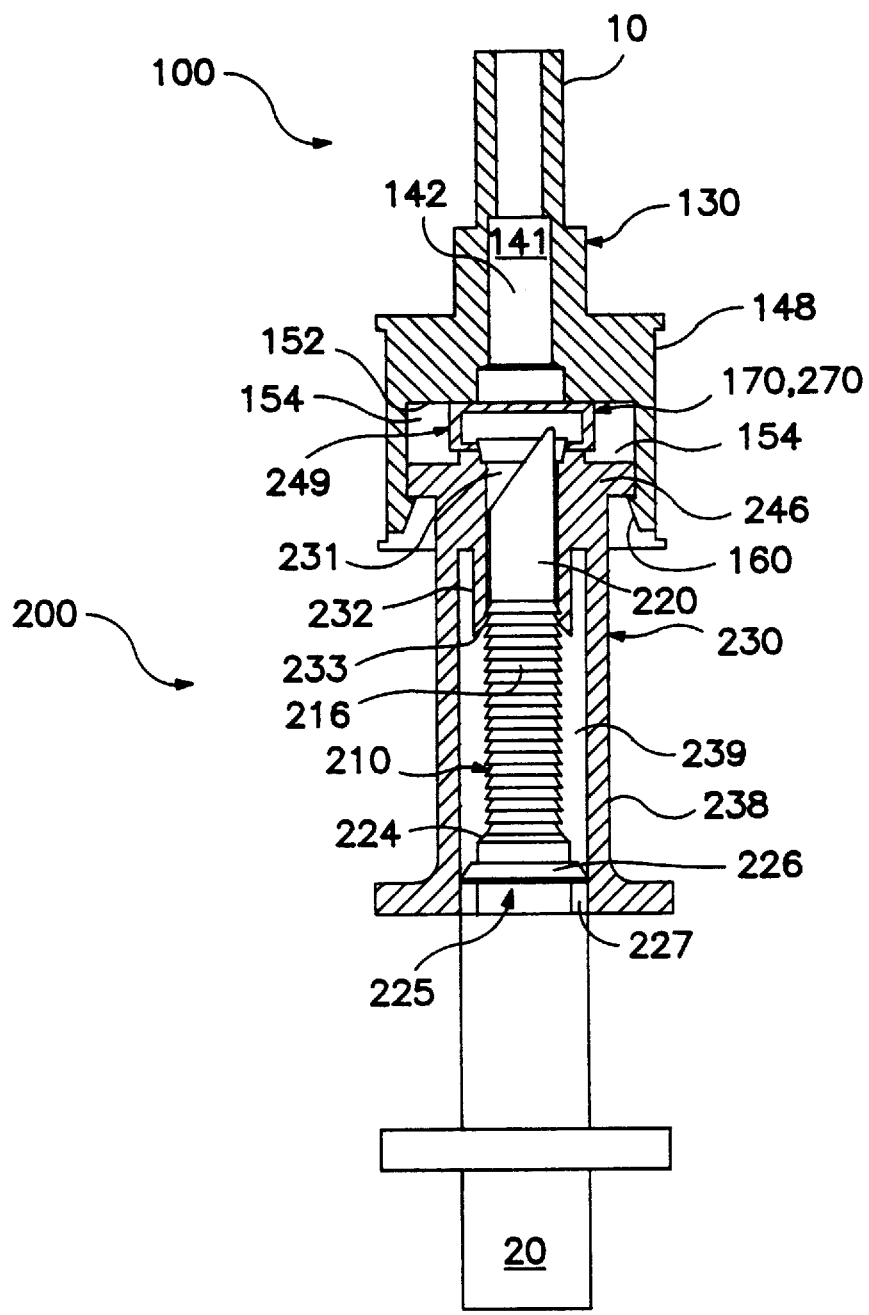
FIG. 6 is an elevation view in partial section of the components of FIG. 1 in partial assembly.
Figure 7:
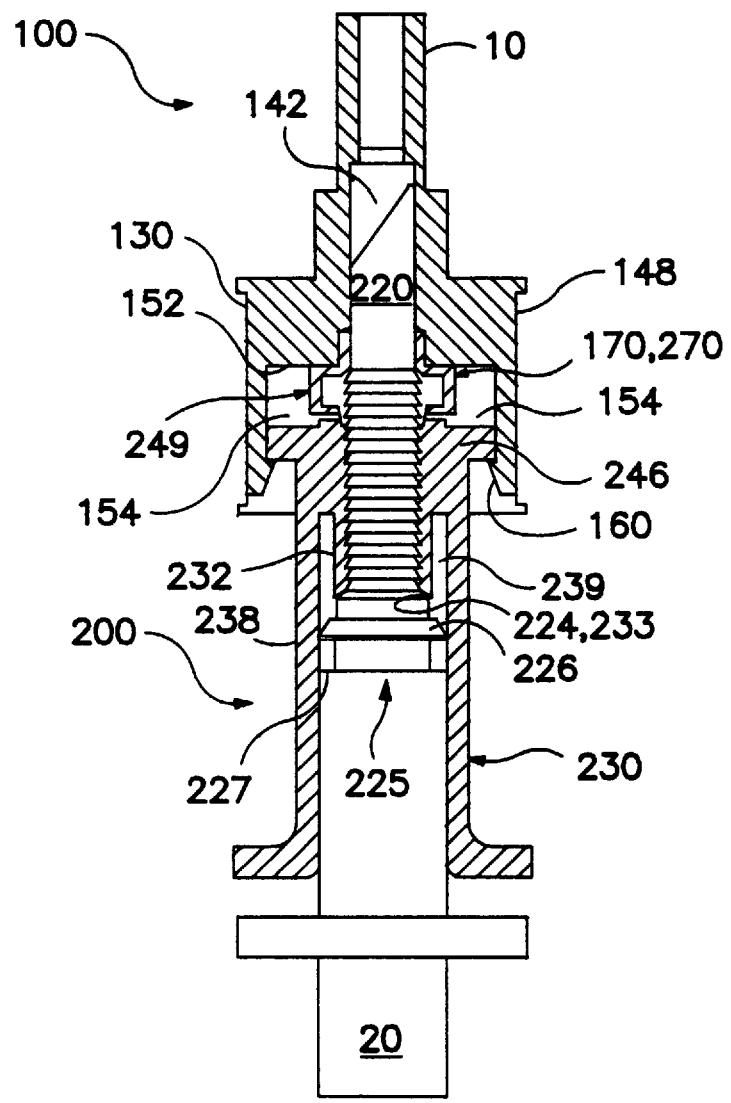
FIG. 7 is an elevation view in partial section, of the components of FIG. 1 in final assembly.

FIGS. 1, 6, and 7 show elevation views of the male connector 200 in different stages of assembly with the female connector 100. FIGS. 1, 6, and 7 comprise views in partial section, as the stem 210 is shown in plain (i.e. non-sectioned) elevation. The male connector 200 generally includes a stem 210 housed in a fitting 230. The male connector 200 may also include a resilient mount 249 having a membrane assembly 270 secured thereto.

The male connector 200 is preferably adapted to contain and conduct isolated fluid communication. Accordingly, the stem 210 is preferably housed within a sealed chamber or aperture 231 defined within the fitting 230. In the illustrative embodiment, the stem 210 is hollow, defining a lumen (not shown) therein. The proximate end of the stem 210 may have a head 220 formed thereon. The head 220 may comprise a piercing element since it may have a sharpened tip. The head 220 may have an aperture providing fluid access between the lumen and the exterior of the stem 210. The stem 210 may also be connected to a fluid conduit section, e.g., the tubing section 20. If the stem 210 and tubing 20 are fabricated as separate components, the tubing 20 may be joined to the base 223 using solvent, bonding or ultrasonic welding for example. Alternatively, the stem 210 and tubing 20 (or other fluid conduit structure) may be molded as an integral part. The stem 210 may also be formed with a ratchet structure, for example beveled annular ribs 216 formed on the external surface of the stem 210. These ribs 216 are shown in plain, non-sectioned elevation in the partially cross sectioned FIGS. 1, 6 and 7. The ribs 216 may circumfuse the external surface of the stem 210. The ribs 216 may be beveled such that they project from the surface of the stem 210, extending distally toward the base 223 of the stem 210 and forming an acute angle with the external surface of the stem 210.

Although the male connector may be variously configured, the illustrated male connector 200 comprises an arrangement of telescoping elements adapted to house at least a portion of the stem 210 within the internal chamber 231 in isolation from contaminants. Thus, by way of illustration, the fitting 230 may have a generally cylindrical sleeve 232 extending from the flange 246. The sleeve 232 defines a bore 234 forming a portion of the internal chamber 231. The stem 210 may register intimately with the sleeve 232. In the illustrated embodiment, a head portion 220 of the stem 210 is housed within the sleeve 232.

The illustrative male fitting 230 may further be constructed with a second outside sleeve 238 concentrically disposed about the first sleeve 232. The concentric sleeves 232, 238 may be connected by any appropriate means. In the representative embodiment, the fitting 230 is formed such that the sleeves 232, 238 and the flange 246 comprise integral portions of the fitting 230. Preferably, the outside sleeve 238 isolates both the stem 210 and the interior bore 234 of the inside sleeve 232 from exposure to the ambient. Thus, the axial length of the inside sleeve 232 may be shorter than the axial length of the outside sleeve 238. The remainder of the body of the stem 210 may be housed within an interior bore 239 defined within the outside sleeve 238.

The stem 210 may include a telescoping seal assembly adapted to mate in telescoping engagement with one or both of the sleeves 232, 238 to isolate and preferably seal the internal chamber 231. Generally, the telescoping seal assembly may be adapted to engage either sleeve, internally or externally. In the exemplary embodiment, the seal assembly 225 may mate in telescoping engagement at least with the interior bore 239 defined in the outside sleeve 238. The telescoping assembly may include elastomeric or deformable elements which intimately engage the walls of the interior bore 239. As shown in the representative embodiment of FIGS. 1, 6, and 7, the illustrative telescoping assembly 225 may include a plunger 226 and an O-ring 227 which fits within a groove in the plunger 226. Preferably the plunger 226 and/or the O-ring 227 tightly engage the inside wall of the outside sleeve 238. This engagement advantageously isolates the interiors of both the inside and outside sleeves 232, 238 from the ambient.

The telescoping seal assembly may also mate with the inside sleeve 232 to seal the internal chamber 231. For this purpose, the distal end of the sleeve 232 may be formed with a rim 233. The rim 233 may assume a tapered form as shown. The telescoping seal assembly 225 may additionally include a shoulder 224 formed on a base 223 of the stem 210. The shoulder 224 may have a tapered form adapted to mate with that of the rim 233, providing another seal for the chamber 231.

Although the illustrated embodiment comprises an arrangement of telescoping elements, the male connector may include other arrangements for advancing the stem. For example, a screw mechanism with a ratchet may be mounted between the outer sleeve and stem. The stem could then be advanced by rotating the screw mechanism.

As exemplified in the plan view of the male connector 200 in FIG. 3, the flange 246 may be generally annular, circumfusing and extending radially from the sleeve 232. The flange 246 may be formed with the grooves 248. As mentioned above, the engagement of the tongues 158 of the female connector 100 in the grooves 248 of the male connector 200 is part of one possible structure for coupling the connectors 100, 200. This coupling is shown in an initial stage of engagement in FIG. 6.

In an important aspect of the invention, the female and male connectors may form a resilient coupling mechanism for engaging these connectors in biased opposition. Though this resilient coupling mechanism may be fashioned in a variety of ways, in the exemplary embodiment, this coupling mechanism may include the resilient mount 249. A representative construction for the resilient mount 249 is detailed in the sectioned elevation view of FIG. 4. The mount 249 serves as a seat which has at least one of the membrane assemblies secured thereon and which is at least axially resilient (e.g. at least resilient along an axis of the sleeve 232). The resilient mount 249 may be disposed generally between the female and the male connectors 100, 200, providing antagonism between the coupled connectors. The resilient mount 249 could be connected to the female connector 100. However, in the illustrated embodiment the resilient mount 249 is connected to the male connector 200.

Figure 4:
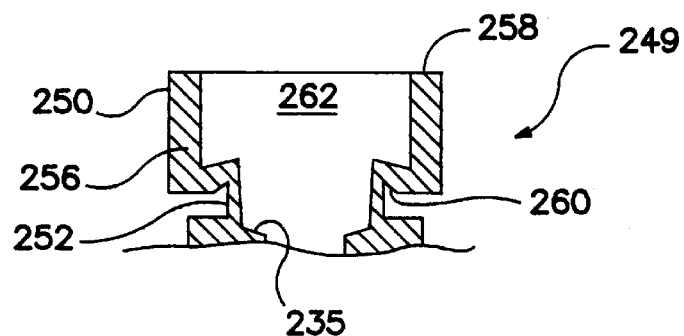
FIG. 4 is an elevation in cross section of a resilient mount in the embodiment of FIG. 1.

As best shown in FIG. 4, the mount 249 may include a resilient neck 252 connecting a hub 250 to the flange 246. The exemplary hub 250 defines a sealable seat surrounding an opening into the chamber 231. Thus, the hub 250 may have a wall 256 defining a well 262. The wall 256 may have an annular plan form, for example, as best shown in FIG. 3. The well 262 communicates with the bore 234 in the sleeve 232. Together, the illustrative bore 234 and well 262 form the internal chamber 231. The wall 256 may further have a rim 258. This rim 258 forms the sealable seat circumfusing the well 262 which accesses the chamber 231. The membrane assembly 270 is preferably secured to the rim 258, enclosing the internal chamber 231.

As detailed particularly in FIG. 4, the neck 252 may be formed with a joint having a recess or groove, shown generally at 260. The grooved joint 260 connects the neck 252 to the hub 250, on the distal side of the hub. When the connectors 100, 200 are engaged, the grooved joint 260 yields, and the neck 252 is compressed at least axially. Thus, the axial resilience of the mount 249 urges the connectors into biased opposition, maintaining the membrane assemblies 170, 270 in positive contact. As one alternative to the grooved joint 260, the hub may be formed with a thin flange joining the neck.

The resilient mount 249 may be formed as an integral part of the male fitting 230. Thus, the sleeve 232, flange 246, neck 252 and/or hub 250 may be molded integrally for example. In this embodiment, the male fitting 230, like the female fitting 130, is molded as a single part from any suitable polymeric material, for example olefinic compositions such as polypropylene, polyethylene, butadiene; acrylics; polycarbonates; or elastomers.

Preferably, the female and male connectors 100, 200 are interlocked in predetermined relation and are resiliently coupled in antagonistic biased opposition. The coupling structure on each connector may be proportioned relative to the other to produce an antagonistic coupling. As noted above, FIG. 6 shows the tongue-in-groove coupling of the representative female and male fittings 130, 230 in partial assembly. The catches 160 abut the distal surface of the flange 246, interlocking the connectors 100, 200 in predetermined relation to each other. The dimensions of the fittings 130, 230 are preferably proportioned such that when the catches 160 embrace the distal surface of the flange 246, the resilient mount 249, including the hub 250 and neck 252, compresses axially, forces the membrane assemblies 170, 270 into positive contact, and provides biased opposition between the membrane assemblies 170, 270. To protect the resilient mount 249, shoulders 154a–154d, seen particularly in FIGS. 1 and 2, may be formed preferably on the flange 148 of the female connector 100. These shoulders may serve as stops limiting the compression of the mount 249 by ensuring a minimum spacing between the connectors. Alternatively, the mount 249 may be constructed such that it can tolerate compression that is limited by contact between the flanges 148, 246 and the hub 250.

Prior to coupling the connectors 100, 200, the proximate, opposing surfaces of the membrane assemblies 170, 270, are exposed to the ambient environment. Upon coupling, these opposing surfaces are forced into positive contact with each other due to the biased opposition imposed by the resilient mount 249. In a principal feature of the invention, this positive contact is maintained as long as the connectors 100, 200 are coupled. Through this positive contact, the contacting surfaces of the membrane assemblies 170, 270 cover each other, isolating them from the ambient.

Figure 5A:
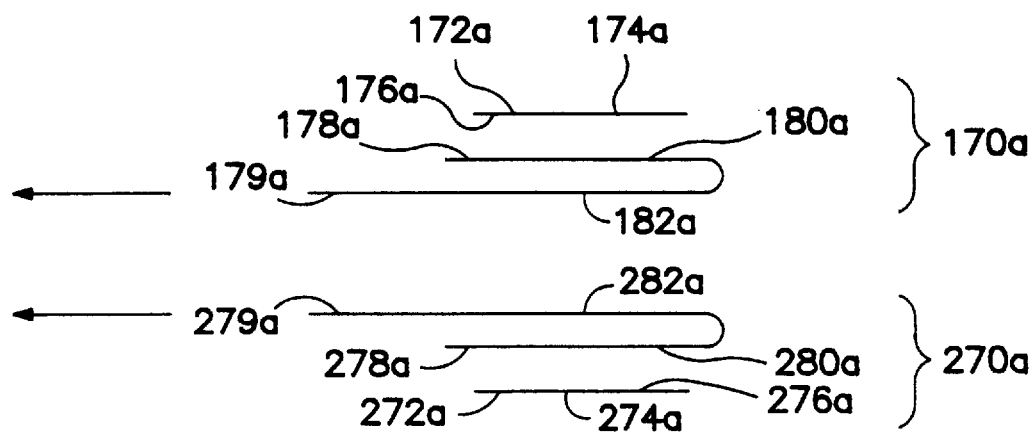
FIG. 5a is a schematic of one embodiment of a membrane assembly according to the invention.
Figure 5B:
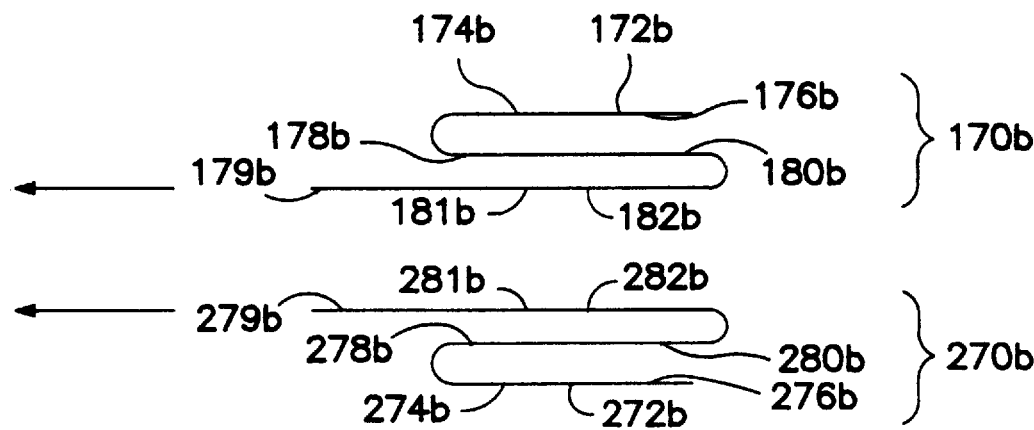
FIG. 5b is a schematic of another embodiment of a membrane assembly according to the invention.

The membrane assemblies of the connectors may be variously configured and may. be identical or not. FIGS. 5a and 5b are schematics showing different embodiments for the membrane assemblies. In a principal aspect of the invention, each membrane assembly includes at least two layers or surfaces. The first comprises a removable contamination containment surface. Initially, this surface comprises the proximate surface of each respective membrane assembly, i.e., the surface nearest and facing the opposing connector. The second surface of each membrane assembly comprises a protected sealing surface. This surface is protected and preferably isolated from the ambient environment and from contaminants present in the ambient environment. At least initially, prior to the stage of inserting the stem into the female connector, the sealing surface seals the chamber defined within each respective fitting. In FIGS. 5a and 5b, in the membrane assembly 170 of the female connector 100, the sealing surface and the contamination containment surface are denoted by 174 and 182, respectively. in the membrane assembly 270 of the male connector 200, the sealing surface and the contamination containment surface are denoted 274 and 282, respectively.

The layers or surfaces of the membrane assemblies may be variously configured. In the exemplary embodiment of FIG. 5a, the contamination containment surface comprises a surface of a cover layer which may be completely removed from the membrane assembly. This exposes a separate underlying sealing layer, having the sealing surface as one of its surfaces. In the embodiment of FIG. 5b, the contamination containment surface comprises a portion of a surface of a cover layer which is folded in a serpentine configuration. This cover layer may be unfolded, exposing a protected cover layer portion, or may be removed completely, exposing a separate sealing layer.

FIG. 5a shows one preferred embodiment of the membrane assemblies 170a, 270a. Each membrane assembly 170a, 270a, in the illustrative embodiment, comprises two separate layers. The membrane assembly 170a has a cover layer 178a serving as a removable protective sheath covering a separate sealing layer 172a. The sealing surface 174a comprises the surface of the sealing layer 172a facing the female flange 148. The contamination containment surface 182a comprises the surface of the cover layer 178a facing the male connector 200.

More particularly, the sealing layer 172a may enclose the chamber 141 defined within the female fitting 130, preferably sealing it. Thus, the sealing surface 174a may be secured to the seat 152, preferably permanently, using any of the techniques discussed above, e.g. ultrasonic welding. In this embodiment the sealing layer 172a is laid flat over the opening to the chamber 141 and because the sealing layer 172a has no folds, it has only two surfaces, the sealing surface 74a and an intermediate surface 176a. Also preferably, the sealing layer 172a may comprise a material which precludes the passage of bacteria therethrough. This material my be porous, preferably having a pore rating of about 0.2 µm or less. Alternatively, the sealing layer 172a may comprise a material which is impervious to both liquid and gas. Accordingly, in one key function the membrane assembly 170a isolates a portion of the fluid path from the ambient environment and from contaminants in the ambient environment since the sealing layer 172a seals the chamber 141.

In the illustrated embodiment, the cover layer 178a is disposed over the sealing layer 172a in a single fold configuration. The exemplary cover layer 178a has a pull tab 179a (shown also in FIG. 2), an intermediate surface 180a and the contamination containment surface 182a. When the cover layer 178a is attached to the sealing layer 172a, the intermediate surface 176a of the sealing layer 172a and the intermediate surface 180a of the cover layer 178a are interfaced in intimate contact. The cover layer 178a is preferably removably attached to the sealing layer 172a in any suitable manner. The sealing layer 172a and the cover layer 178a can be attached together by heat sealing the perimeter of the intermediate surfaces 176a, 180a, for example. Alternatively, the intermediate surface 180a, but not the contamination containment surface 182a, of the cover layer 178a has a tackiness or an adhesive which releasably holds the cover layer 178a to the sealing layer 172a but which entirely remains with the cover layer 178a when the cover layer 178a is removed from the sealing layer 172a. The contamination containment surface 182a of the cover layer 178a and the intermediate surface 176a of the sealing layer 172a thus remain free of adhesive, preventing ambient contaminants from being attracted to and held by either surface. Further, because the intermediate surface 176a of the sealing layer 172a remains free of adhesive, there is no risk that the adhesive will leach into fluid flowing through the connector assembly.

Prior to coupling the female and male connectors 100, 200, the contamination containment surface 182a is exposed to the ambient environment. Preferably, the cover layer 178a also comprises a material, such as glassine paper, which precludes the passage of bacteria therethrough. Accordingly, while the cover layer 178a is attached to the sealing layer 172a, it isolates the sealing layer from the ambient. In another key function of the membrane assembly 170a, the cover layer 178a protects the sealing layer 172a, isolating it from contact with other surfaces, or surface area portions, or the ambient. More particularly, the cover layer 178a may be advantageously folded as shown so that the intermediate surface 180a intimately interfaces with the sealing layer 172a and protects the sealing layer 172a from even the exposed contamination containment surface 182a.

The membrane assembly 270a of the male connector 200 has a construction analogous to that of the membrane assembly 170a. The membrane assembly 270a has a sealing layer 272a and a cover layer 278a. The sealing surface 274a comprises the surface of the sealing layer 272a facing the male flange 246. The contamination containment surface 282a comprises the surface of the cover layer 278a facing the female connector 100.

The sealing layer 272a seals the well 262, and thus the chamber 231 defined within the male fitting 230. Accordingly, the sealing surface 274a is secured to the rim 258 of the axially resilient hub 250. The sealing surface 274a may be secured, preferably permanently, using any of the techniques outlined above, e.g. ultrasonic welding. The sealing layer 272a may be laid flat over the well 262. Because the sealing layer 272a has no folds ir. this embodiment, it has two surfaces, the sealing surface 274a and an intermediate surface 276a. The sealing layer 272a may be impervious to gas or liquid or may comprise a porous, hydrophobic material which precludes the passage of bacteria therethrough. The sealing layer 272a thus isolates the chamber 231 from the ambient and from contaminants entrained in the ambient.

As in the female connector, the cover layer 278a may similarly be removably attached to the sealing layer 272a.

This cover layer 278a may also be disposed over the sealing layer 272a in a single fold configuration. The exemplary cover layer 278a has a pull tab 279a (shown also in FIG. 2), an intermediate surface 280a and the contamination containment surface 282a. When the cover layer 278a is attached to the sealing layer 272a, the intermediate surface 276a of the sealing layer 272a and the intermediate surface 280a of the cover layer 278a are interfaced in intimate contact. Accordingly, while the cover layer 278a is attached to the sealing layer 272a, it isolates the sealing layer from the ambient and from contact with other surfaces exposed to the ambient.

In each of the previous embodiments of the membrane assemblies 170, 270, the cover layer 178, 278 intimately contacts the sealing layer 172, 272. However, the membrane assembly may alternatively be configured with the sealing layer spaced from the cover layer. For example, the cover layer may be removably attached to the flange of the connector, enclosing the chamber, while the sealing layer is spaced from the cover layer and positioned within the chamber sealed to the walls of the bore.

The antagonistic coupling of the connectors created by the tongue-in-groove engagement and the axially resilient mount 249 urges the respective contamination containment surfaces 182a, 282a, into biased opposition. This resilience ensures positive contact between the contamination containment surfaces 182a, 282a as long as the connectors 100, 200 are coupled.

Preferably, the fittings 130, 230, and thus the surfaces within the fittings defining the chambers 141, 231, may be sterilized either before or upon assembly with each other. Each of the sealing surfaces 174a, 274a seals its respective chamber 141, 231, isolating the chamber from the ambient and contaminants entrained therein.

According to a principle aspect of the invention, each of the contamination containment surfaces 182a, 282a can be removed while maintaining these surfaces in positive contact. Once the connectors 100, 200 are coupled, they form a housing and the pull tabs 179a, 279a of the cover layers 178a, 278a preferably abut each other and extend in the same direction to the exterior of the housing. For example, in the embodiment illustrated in FIG. 5a, the pull tabs 179a, 279a extend out of the channel of the U-shaped bracket 148 (i.e., into or out of the plane of the drawing page), beyond the assembly of the two connectors 100, 200. The pull tabs 179a, 279a can be pulled by hand,-pinching the tabs together with two fingers. The tabs 179a, 279a are most preferably pulled simultaneously, while maintaining the contamination containment surfaces 182a, 282a in biased contact. When the tabs are pulled together, the biased opposition of the resilient coupling maintains the positive contact between the contamination containment surfaces 182a, 282a. Each contamination containment surface 182a, 282a may trap and isolate any contaminants on the other. Even as the cover layers 178a, 278a are removed, the resilient mount 249 urges the contamination containment surfaces 182a, 282a into positive contact with each other. Also, a bacteriostatic or bacteriocidal compound or layer could be disposed on either or both contamination containment surfaces 182a, 282a. As the cover layers 178a, 278a are removed, each contamination containment surface 182a, 282a is pulled away from the respective sealing layer 172a, 272a by virtue of the advantageous fold configuration. Thus, in another key feature the membrane assemblies 170a, 270a isolate both the fluid path and surfaces intersecting the fluid path, e.g., the intermediate surfaces 176a 276a at the sealing layers 172a, 277a, from the ambient and surfaces exposed to the ambient, e.g., contamination containment surfaces 182a, 282a.

In addition to being axially resilient, the resilient mount 249 is preferably flexible enough to tilt laterally or rock as the cover layers 178a, 278a are removed. Thus, as the cover layers 178a, 278a are removed, the hub 250 instantly urges the protected intermediate surfaces 176a, 276a of the sealing layers 172a, 272a into positive contact, virtually preventing contamination of these surfaces.

Each contamination containment surface 182a, 282a isolates the other, trapping therebetween any contaminants incident on the surfaces from the exposure of these surfaces to the ambient. The membrane assemblies 170a, 270a isolate both internal chambers 141, 231, and the fluid path portion defined within the stem 210, from the ambient. Further, the membrane assemblies 170a, 270a isolate both internal chambers 141, 231, and the fluid path portion defined within the stem 210, from surfaces exposed to the ambient, e.g., from the contamination containment surfaces 182a, 282a. When the two connectors 100, 200 are coupled and the cover layers 178a, 278a are removed, only surfaces which were previously isolated define or intersect the fluid flow path.

In the embodiment of FIG. 5b, each membrane assembly 170b, 270b comprises at least one sheet arranged in a serpentine fold configuration. Each fold defines a portion of the sheet forming a new layer. Thus, the membrane assembly 170b can comprise a single sheet having one portion forming the sealing layer 172b. Another portion of the sheet after the first fold in the serpentine configuration forms a first cover layer 178b. Yet another portion of the sheet after the second fold in the serpentine configuration forms a second cover layer 181b.

More particularly, the sheet portion forming the sealing layer 172b has two surfaces, a sealing surface 174b and an intermediate surface 176b. Analogous to the embodiment of FIG. 5a, the sealing surface 174b may be secured to the seat 152 of the female fitting 130, preferably permanently. Preferably, the sealing layer 172b comprises a material which precludes the passage of bacteria. Thus the membrane assembly 170b isolates a portion of the fluid path from the ambient and contaminants present in the ambient since the sealing layer 172b seals the chamber 141.

The first cover layer 178b may be removably attached to the sealing layer 172b as previously discussed with respect to the embodiment shown in FIG. 5a. The first cover layer 178b has an intermediate surface 180b. When the membrane assembly 170b is folded, the intermediate surface 176b of the sealing layer 172b and the intermediate surface 180a of the first cover layer 178b are interfaced in intimate contact.

The second cover layer 181b may be disposed over the first cover layer 178b. The second cover layer 181b has a pull tab 179b and a contamination containment surface 182b. The contamination containment surface 182b comprises the surface of the membrane assembly 170b most proximate to the opposing male connector 200. Prior to coupling the female and male connectors 100, 200, the contamination containment surface 182b is exposed to the ambient. Preferably, the membrane assembly 170b comprises a homogeneous membrane sheet. Thus, both cover layers 178b, 181b also preclude the passage of bacteria therethrough. Accordingly, while the cover layers 178b, 181b are protectively disposed over the sealing layer 172b, they isolate the sealing layer from the ambient contaminants and from surfaces exposed to the ambient.

In the embodiment of FIG. 5b, the membrane assembly 270b of the male connector 200 can be constructed in a fashion analogous to the membrane assembly 170b of the female connector 100. Reference numerals for components of the membrane assembly 270b are analogous to the numerals for the membrane assembly 170b, except that the 200 series is used.

In use, the hollow stem 210 forms an isolated portion of the fluid communication path. On the proximate side of the internal chamber 231 of the male connector 200, the membrane assembly 270 preferably seals the hollow stem 210 therein. On the distal side of the chamber 231, the telescoping seas assembly 225 preferably seals the stem 210 therein. As exemplified in FIG. 7, in final assembly the stem 210 is adapted to bridge the chambers 141, 231. Accordingly, the stem 210 is free to move axially within the bore 234, toward the proximate end of the male fitting 230.

To establish fluid communication between the internal chambers 141, 231, the connectors 100, 200 are first positively interlocked. The connectors 100, 200 may be interlocked by the tongue-in-groove coupling described above, for example. The resilient mount 249 is then compressed and urges the cover layers of the membrane assemblies 170, 270 into positive contact against each other. The cover layers 178, 278 can then be removed by pulling the tabs 179, 279. The biased opposition provided by the resilient mount 249 simultaneously urges the protected sealing layers of the membrane assemblies 170, 270 into positive contact against each other.

The stem 210 then can be advanced within the male fitting 230 by hand, for example. The stem 210 may advance within the sleeves 232, 238 until the rim 233 formed on the distal end of the inside sleeve 232 abuts the shoulder 224 formed on the stem 210. The mating tapered surfaces of the rim 233 and the shoulder 224 provide yet another seal isolating from the ambient the internal chamber 231 as well as the stem portion or head 220 therein. This abutment also serves as a stop, ultimately limiting the axial travel of the stem 210. The advance of the stem 210 is sufficient to allow the stem 210 to pierce at least the sealing layer 172, 272 of each membrane assembly 170, 270, respectively. The head 220, which comprises a piercing element, may thus have a pointed form for example, adapted for this penetration. By inserting the stem 210 into the female fitting 130, fluid communication is established between the female and male connectors 100, 200. Thus, the tubes 10, 20 are joined in fluid communication, and a single fluid path is formed through the connector assembly.

Preferably, once the stem 210 is inserted into the female fitting 130, an axial restraint resists retraction of the stem 210. Such a restraint preferably prevents altogether the retraction of the stem 210. This restraint is implemented in the illustrated embodiment by a ratchet or locking structure. The inside sleeve 232, including the tapered form of the rim 233 cooperates with the angle of the beveled ribs 216 to allow axial advance of stem 210 toward the female connector 100 with sufficient resistance to prevent accidental or incidental movement of the stem 210. The distal end of the inside sleeve 232 may further be formed with a lip or catch 236 depending radially inward within the bore 234. Upon attempting retraction of the stem 216, the beveled ribs 216 may engage the catch 236. This engagement prevents axial retraction of the stem 210, locking the stem within the female fitting 130. The ratchet structure may additionally include engagement of the beveled ribs 216 by an internal shoulder 235 (shown in FIG. 4) formed in the bore 234 of the sleeve 232, for example.

The axial restraint may also be implemented or augmented by the frictional telescoping engagement of mating parts. This includes the telescoping engagement of the plunger 226 and/or O-ring 227 within the bore 239. Also, both the head 220 of the stem 210 and the bore 142 defined within the female fitting 130 may comprise mating tapered forms. Accordingly, the head 220 may be lodged in frictional telescoping engagement within the internal chamber 141 of the female connector 100, sealing the stem 210 within the female connector 100 and resisting disengagement.

In another representative embodiment shown in FIGS. 8 and 9, components corresponding to the previous embodiment are denoted with the same reference numerals. The illustrated seal assembly 225 may further include a frangible flange 243, in addition to the plunger 226. The outside sleeve 238 may have a seat assembly 240 formed at the distal end thereof. The frangible flange 243 may be fixed to the seat assembly 240 by any appropriate means, e.g. by bonding or welding, and may thus seal the interior bore 239 defined within the outside sleeve 238. The seat assembly 240 may include a rim 242 which abuts the frangible flange 243 when the latter is fixed to the seat assembly. Preferably, the frangible flange 243 comprises an element which may be severed or broken. more particularly, the frangible flange 243 may comprise a thin wall for example. Further, the frangible flange 243 may have a cleavage or crease formed on either side of the flange. The position of this crease would coincide with the area where the rim 242 which abuts the frangible flange 243. Also, the rim 242 may advantageously form a sharp edge.

The assembly of connectors 100, 200 of the embodiment of FIGS. 8 and 9 may operate similarly to the earlier embodiment. After the connectors 100, 200 are coupled and the removable cover layers are removed from the membrane assemblies 170, 270, the stem 210 can be advanced. The stem 210 may be forcibly advanced by hand such that the flange 243 is severed or broken against the rim 242. As the stem 210 is advanced, the plunger 226 moves along the wall of the bore 239. The plunger 226 may again be advantageously formed from a compressible material, for example an elastomeric material. Contact between the plunger 226 and the wall of the bore 239 provides a secure seal from the ambient for both bores 239, 234 and the internal chamber 231. Also, part of the frangible flange 243 remaining with the plunger 226 preferably comprises a material which may yield, compressing radially or folding at its periphery, for example. Thus, the remaining portion of the severed flange 243 may initially enter and advance within the bore 239 while constantly maintaining sealed contact with the tapering wall defining the bore 239.

In summary, in this embodiment of the connector assembly, at least four mechanisms advantageously cooperate to isolate from the ambient the distal end of the internal chamber 231. originally, prior to advancing the stem 210, the frangible flange 243 may be fixed to the seat assembly 240, sealing the bore 239. Once the stem 210 is advanced, the periphery of the remaining portion of the frangible flange 243 intimately contacts the wall defining the bore 239. Similarly, the plunger 226 also intimately contacts the tapering wall of the bore 239. Finally, the abutting tapered surfaces of the rim 233 of the inside sleeve 232 and shoulder 224 of the stem 20 mate to seal the bore 234.

As with all illustrated embodiments herein, a number of variations in the illustrated constructions are envisioned. For example, another embodiment for the female connector 100 is illustrated in FIG. 10, where analogous components have the same reference numerals. In this embodiment, the counter bore 144 is closed at a blind end by a pierceable septum 147 and the septum 147 may comprise an integral part of the flange 150. Thus, the chamber 141 defined within the tubing 10 is sealed by both the membrane assembly 170 and the septum 147. The septum 147 may provide additional security in sealing the chamber 142 from ambient contaminants and from surfaces previously exposed to the ambient. The septum 147 may also resist the pressure of the fluid in the tubing section better than the membrane assembly 170. When the female and male connectors 100, 200 are coupled, the stem 210 can be axially advanced through the sleeve 232 to pierce three elements: the membrane assembly 270 of the male connector 200 and the membrane assembly 170 and the septum 147 of the female connector. In one possible mechanism for axial restraint of the stem, a throat may be formed where the septum is pierced, whereby the stem registers in an intimate friction fit within the throat.

Other variations are also envisioned. For example, where the female connector and fluid conduit comprise separate components, they could be connected by a variety of other means, e.g. mating threaded fittings. Alternatively, the bracket may be attached to a sleeve, either formed integrally with the bracket or otherwise connected thereto. This sleeve may be connected to a section of tubing through telescopic engagement, i.e. a coaxial friction fit wherein one member is inserted within the other, with friction between the two members retaining the coupling. In another variant construction for the female connector, the two bores and the tubing can be variously configured. In the exemplary embodiment of FIGS. 1–3 these components are generally cylindrical. Alternatively, they may be formed with cross sections of various geometries, for example rectangular or elliptical.

A number of variations are envisioned in the construction of the male connector. The hub and/or sleeve may assume cross sections of any suitable form, for example rhomboid or trapezoidal. Also, the sleeve, flange and/or hub, for example, can be molded or machined as separate parts, each with mating threads. The sleeve can also be constructed as separate, hollow telescoping sections housing a helical spring, for example. This may serve as a substitute for the illustrated construction of the resilient mount. The telescoping sections of the sleeve can be dimensioned to allow easy axial reciprocation of one half within the other. The spring would provide the resilience necessary to couple the connectors in biased opposition, maintaining positive contact between membrane assemblies. If the spring is helical, it can be sized such that the stem can be loosely housed, allowing for axial displacement within the helix. In another alternative to the illustrated construction of the resilient mount, the male fitting can alternatively be formed or machined as an integral piece from a post of elastomeric material. This post would be bored to make it a hollow sleeve, and may be constructed without a separate hub piece. Alternatively, a separate elastomeric hub can be mounted on a sleeve piece.

The axial resilience in the coupling can alternatively be provided by using a deformable or resilient material for one or both sealing layers of the membrane assemblies. The resilience and thickness in the sealing layer should provide the compliance and clearance necessary to urge the contamination containment surfaces into positive contact. Hence, the sealing layers may be made thick relative to the cover layers. The removable cover layers may.be made thin relative to the sealing layers to make removal easy while assuring positive contact of interfacing intermediate surfaces.

The illustrated structure for coupling the female and male connectors can also be modified. The exemplary tongue-in-groove coupling can be replaced with any coupling, preferably an interlocking structure which locks or becomes non-separable after coupling. A rabbeted coupling, for example, can be implemented by forming one connector with a groove or recess cut out of an edge or face of its body. The other connector can be formed with a boss or rib having a shape that mates with that recess. In another alternative coupling, the female and male connectors can comprise any suitable form of mating threaded fittings.

Several alternative constructions for the axial restraint of the stem are possible. An axial restraint can be implemented by several embodiments of a friction fit, for example. The counter bore within the female fitting may be proportioned to accommodate any flaps formed when the membrane assemblies are pierced. As the stem passes, the flaps can be pressed radially against the inside wall of the counter bore. A tight friction fit may be formed with the flaps of the pierced membrane caught between the stem and the wall of the counter bore. Withdrawal of the stem from the female fitting may be prevented in part by friction. Forward edges of the membrane flaps may also engage the annular beveled ribs, preventing withdrawal of the stem.

In another alternative for the axial restraint, the stem and the male fitting may be formed as telescoping parts, coaxially engaging in a friction fit. These components may have tapered or conic sections, for example. Additionally or alternatively, these components may be formed with a rabbeted structure, e.g., a rib or lug may be formed on one component to engage in a mating recess formed in the other.

In the illustrated assembly of female and male connectors it may be desirable to ensure that accidental or incidental insertion of the Stem through the membrane assemblies is prevented. Accordingly, the connector assembly can additionally be equipped with a mechanism initially preventing insertion of the stem. In one embodiment, this mechanism may be implemented by forming the proximate end of the stem with a relatively dull nipple rather than a head with a sharp tip. Additionally, the sealing and cover layers within a given membrane assembly could Comprise different materials, e.g., materials which strongly resist being pierced by the stem. The nipple may also have a form which can penetrate one of the sealing or cover layers, but not the other. In another embodiment, this mechanism may comprise a cam structure. The connector housing the stem, e.g. the male fitting 230 in the illustrated embodiments, may have a slot formed in the sleeve and the stem may be formed with a lug which serves as a cam. The cam can prevent axial advance of the stem when it abuts the rim of the sleeve, but upon twisting the stem to align the cam with the slot in the sleeve the stem 210 is freed from the locking action of the cam. The stem may then be inserted into the female connector, piercing the membrane assemblies.

I claim:

1. A connector assembly comprising:
   (a) a first fitting defining a first aperture;
   (b) a second fitting defining a second aperture;
   (c) a first membrane assembly sealing the first aperture;
   (d) a second membrane assembly sealing the second aperture;
   (e) an axially resilient seat disposed between the first and second fittings and urging the first and second fittings into biased opposition, thereby maintaining the first and second membrane assembly in positive contact, the axially resilient seat including a first section comprising a substantially cylindrical hub having a first diameter and defining a rim upon which the first membrane assembly is disposed and a resilient connector connecting the first section to the first fitting and providing an axially resilient connection between the first section and the first fitting, the resilient connector including a neck having a second diameter less than the first diameter, the resilient seat and the first fitting comprising a single, integral molded structure formed from a polymeric material.

2. The connector assembly according to claim 1, wherein the resilient connector further comprises a grooved joint cooperatively arranged with the cylindrical neck.

3. A connector assembly comprising:

a first fitting defining a first aperture;

a second fitting defining a second aperture;

a first removable contamination containment layer overlying the first aperture;

a second removable contamination containment layer overlying the second aperture; and an axially resilient seat disposed between the first and second fittings, the first and second fittings being couplable to provide positive contact between the first and second removable contamination containment layers, the axially resilient seat including a substantially cylindrical hub having a first diameter and a neck having a second diameter less than the first diameter, the hub defining a rim and the first contamination containment layer removably contacting the rim of the hub.

4. A connector assembly comprising:

a first fitting defining a first aperture;

a second fitting defining a second aperture;

a first removable contamination containment layer overlying the first aperture;

a second removable contamination containment layer overlying the second aperture; and an axially resilient seat disposed between the first and second fittings, the first and second fittings being couplable to provide positive contact between the first and second removable contamination containment layers and the axially resilient seat including a substantially cylindrical hub and a neck, wherein the hub defines a rim and the first contamination containment layer removably contacts the rim and wherein at least one of the hub and neck is axially compressible.

5. A connector assembly comprising:

a first fitting defining a first aperture and including a first removable contamination containment layer overlying the first aperture;

a second fitting defining a second aperture and including a second removable contamination containment layer overlying the second aperture;

a resilient coupling mechanism positioned between the first and second fittings at the first and second apertures;

an interlock mechanism including at least one tongue extending between the first and second fittings and adapted to engage a corresponding surface to interlock the first and second fittings, the first and second fittings being couplable to provide positive contact between the first and second contamination containment layers; and a stem member mounted in the first fitting and including a head axially movable through the first fitting into the aperture of the second fitting.

6. The connector assembly according to claim 5, wherein the first fitting includes a wall defining a bore and the stem member is axially slidable within the bore, wherein the stem member includes a plunger sealingly engaging the wall, and wherein the connector assembly further comprises a seal positioned between the wall and the stem member.

7. The connector assembly according to claim 5, wherein the first fitting includes a sleeve defining a bore, the stem member is axially slidable within the bore and the connector assembly further comprises a rachet mechanism arranged between the sleeve of the first fitting and the stem member to resist retraction of the stem member from the second fitting.

8. The connector assembly according to claim 5, wherein the first fitting includes a first wall defining a first bore and a second wall defining a second smaller bore and the stem member includes a plunger mounted at an end of the stem member opposite that of the head, wherein the plunger sealingly engages the first wall and is axially slidable within the first bore and the stem member and head are axially slidable within the second bore, and wherein the connector assembly further comprises a seal disposed between the stem member and the first wall.

9. The connector assembly according to claim 5, wherein the first fitting includes a first sleeve defining a first bore and a second sleeve defining a second smaller bore, the stem member being axially slidable within the second bore, and wherein the connector assembly further comprises a seal disposed between the stem member and the first sleeve and a rachet mechanism arranged between the stem member and the second sleeve.

10. The connector assembly according to claim 5, wherein the aperture of the second fitting includes a bore and the stem member is insertable into the bore, the stem member and the bore having mateable tapered forms, whereby the stem member can be frictionally engaged in the bore of the second fitting.

11. The connector assembly according to claim 10, wherein the second fitting further includes a larger counterbore communicating with the bore in the second fitting, the counterbore opening at the second aperture onto a seat and the second removable contamination containment layer contacting the seat.

12. The connector assembly according to claim 5, wherein the resilient coupling mechanism includes a first section comprising a substantially cylindrical hub having a first diameter and defining a rim, and a second section coupling the first section to the first fitting and providing an axially resilient connection between the first section and the first fitting, the second section including a neck and having a second diameter less than the first diameter.

13. The connector assembly according to claim 12, wherein the resilient coupling mechanism is attached to the first fitting and the first removable contamination containment layer contacts the hub of the resilient coupling mechanism.

14. The connector assembly according to claim 5, wherein the interlocking mechanism comprises a plurality of tongues extending from the second fitting, each tongue including a catch and a taper formed at a proximate end of the tongue, and wherein the interlock mechanism further comprises a plurality of grooves and corresponding surfaces, the tongues registering within the grooves and the catches abutting the corresponding surfaces.

15. The connector assembly according to claim 5, wherein the wherein the interlocked first and second fittings force the first and second removable contamination containment layers into contact, and wherein the connector assembly further comprises a stop positioned between the first and second fittings.

16. The connector assembly according to claim 5, wherein the stem member and the first fitting comprise a telescoping arrangement.

17. The connector assembly according to claim 14, wherein the stem member includes a locking portion.

18. The connector assembly according to claim 5, wherein the first and second contamination containment layers are removable and are arranged to be removed after the first fitting is coupled to the second fitting.

19. The connector assembly according to claim 18, wherein the first and second removable contamination containment layers each comprise a tab.

20. A connector assembly comprising:
a first fitting defining a first aperture and including a first sealing layer overlying the first aperture;
a second fitting defining a second aperture and including a second sealing layer overlying the second aperture;
a resilient coupling mechanism positioned between the first and second fittings at the first and second apertures;
an interlock mechanism including at least one tongue extending between the first and second fittings and adapted to engage a corresponding surface to interlock the first and second fittings, the first and second fittings being couplable to provide positive contact between the first and second sealing layers; and
a piercing member mounted in the first fitting and axially movable through the first fitting, through the sealing layers into the aperture of the second fitting.

21. The connector assembly according to claim 20, wherein the resilient coupling mechanism includes a first section comprising a substantially cylindrical hub having a first diameter and defining a rim, and a second section coupling the first section to the first fitting and providing an axially resilient connection between the first section and the first fitting, the second section including a neck and having a second diameter less than the first diameter.

22. The connector assembly according to claim 21, wherein the resilient coupling mechanism is attached to the first fitting and the first sealing layer contacts the hub of the resilient coupling mechanism.

23. The connector assembly according to claim 20, wherein the interlocking mechanism comprises a plurality of tongues extending from the second fitting, each tongue including a catch and a taper formed at a proximate end of the tongue, and wherein the interlock mechanism further comprises a plurality of grooves and corresponding surfaces, the tongues registering within the grooves and the catches abutting the corresponding surfaces.

24. The connector assembly according to claim 20, wherein the wherein the interlocked first and second fittings force the first and second sealing layers into contact, and wherein the connector assembly further comprises a stop positioned between the first and second fittings.

25. The connector assembly according to claim 20, wherein the piercing member and the first fitting comprise a telescoping arrangement.

26. The connector assembly according to claim 25, wherein the piercing member includes a locking portion.

27. A connector assembly comprising:
a first fitting defining a first aperture, and including a first removable contamination containment layer overlying the first aperture;
a second fitting coupled to the first fitting, defining a second aperture, and including a second removable contamination containment layer overlying the second aperture;
a stem member mounted in the first fitting and including a head axially movable into the aperture of the second fitting; and
a breakable or severable element positioned between the first fitting and the stem member and providing resistance to axial movement of the stem member into the second fitting.

28. The connector assembly according to claim 27, wherein the element is sealingly connected between the first fitting and the stem member.

29. The connector assembly according to claim 28, wherein the element comprises a frangible element.

30. The connector assembly according to claim 29, wherein the frangible element comprises a thin wall extending between the stem member and the first fitting.

31. The connector assembly according to claim 30, wherein the first fitting includes a seat assembly and the frangible element is fixed to the seat assembly.

32. The connector assembly according to, claim 31 wherein the seat assembly includes a rim arranged to sever the frangible element as the stem member moves toward the second fitting.

33. The connector assembly according to claim 32, wherein the frangible element includes a cleavage or crease which cooperates with the rim to sever the frangible element.

34. The connector assembly according to claim 33, wherein the rim includes a sharp edge which coincides with the cleavage or crease in the frangible element.

35. The connector assembly according to claim 32, wherein the rim includes a sharp edge.

36. The connector assembly according to claim 32, wherein a portion of the severed flange is attached to the stem member, wherein the first fitting includes a wall defining a bore, the stem member being disposed within the bore, and wherein the severed portion of the flange contacts the wall of the bore as the stem member moves toward the second fitting.

37. The connector assembly according to claim 27, wherein the breakable or severable element seals the stem member.

38. A connector assembly comprising:
a first fitting defining a first aperture and including a first removable contamination containment layer overlying the first aperture;
a second fitting defining a second aperture and including a second removable contamination containment layer overlying the second aperture;
an interlock mechanism including at least one tongue extending between the first and second fittings and adapted to engage a corresponding surface to interlock the first and second fittings, the first and second fittings being coupled to provide positive contact between the first and second removable contamination containment layers;
a stem member mounted in the first fitting and including a head axially movable into the aperture of the second fitting; and
an axial restraint coupled to the stem member to resist retraction of the stem member from the second fitting.

39. The connector assembly according to claim 38, wherein the axial restraint comprises a rachet mechanism including a plurality of ribs mounted between the stem member and the first fitting.

40. A connector assembly comprising:
a first fitting defining a first aperture and including a first sealing layer overlying the first aperture;
a second fitting defining a second aperture and including a second sealing layer overlying the second aperture;

an interlock mechanism including at least one tongue extending between the first and second fittings and adapted to engage a corresponding surface to interlock the first and second fittings, the first and second fittings being coupled to provide positive contact between the first and second sealing layers;

a piercing member mounted in the first fitting and axially movable through the sealing layers into the aperture of the second fitting; and an axial restraint coupled to the piercing member to resist retraction of the piercing member from the second fitting.

41. The connector assembly according to claim 40, wherein the axial restraint comprises a rachet mechanism including a plurality of ribs mounted between the piercing member and the first fitting.

42. A connector assembly comprising:

a first fitting defining a first aperture and including a first removable contamination containment layer overlying the first aperture;

a second fitting coupled to the first fitting, defining a second aperture and including a second removable contamination containment layer overlying the second aperture;

a stem member mounted in the first fitting and including a head axially movable into the aperture of the second fitting; and a ratchet mechanism mounted to the stem member to lock the stem member within the second aperture of the second fitting.

43. The connector assembly according to claim 42, wherein the first fitting includes a sleeve and the stem member includes a stem axially slidable within the sleeve, wherein the stem includes a plurality of ribs circumscribing and extending at an acute angle from the stem, and wherein the sleeve includes a catch engageable with at least one of the ribs to prevent retraction of the stem member.

44. The connector assembly according to claim 42, wherein the ratchet mechanism includes a plurality of ribs and a structure which is engageable with at least one of the ribs, the ribs being fixed to one of the first fitting and the stem member and the engageable structure being fixed to the other of the first fitting and the stem member.

45. The connector assembly according to claim 44, wherein at least one of the ribs and the engageable structure are arranged to provide sufficient resistance to prevent accidental or incidental movement of the stem member.

46. The connector assembly according to claim 44, wherein the stem member includes a stem and the ribs are fixed to the stem.

47. The connector assembly according to claim 46, wherein the ribs circumscribe the stem and extend at an acute angle from the stem.

48. The connector assembly according to claim 46, wherein the first fitting includes a sleeve and the engageable structure includes a catch mounted to the sleeve, the stem being slidably disposed within the sleeve.

49. The connector assembly according to claim 48, wherein the catch comprises a first catch and wherein the first fitting includes a second catch spaced from the first catch and engageable with at least one of the ribs.

50. The connector assembly according to claim 49, wherein the second catch is spaced axially from the first catch.

51. The connector assembly according to claim 42, further comprising a resilient coupling mechanism positioned between the first and second fittings at the first and second apertures, the resilient coupling mechanism comprising a hub and a smaller diameter neck coupled to the hub.

52. The connector assembly according to claim 45, wherein the first removable contamination containment layer contacts the hub.

53. The connector assembly according to claim 43, further comprising a resilient coupling mechanism positioned between the first and second fittings, the coupled first and second fittings compressing the resilient coupling mechanism and forcing the first and second contamination containment layers into contact, and a stop positioned between the first and second fittings to limit compression of the resilient coupling mechanism.

54. The connector assembly according to claim 42, further comprising an interlock mechanism coupling the first and second fittings in a predetermined relation.

55. The connector assembly according to claim 54, wherein the interlock mechanism includes a plurality of tongues extending between the first and second fittings and adapted to engage corresponding surfaces to interlock the first and second fittings.

56. The connector assembly according to claim 42, further comprising a resilient coupling mechanism positioned between the first and second fittings at the first and second apertures and an interlock mechanism locking the first fitting to the second fitting.

57. The connector assembly according to claim 56, wherein the resilient coupling mechanism comprises a hub and a smaller diameter neck resiliently mounted to the hub and connected to the first fitting and wherein the interlock mechanism comprises a plurality of tongues extending between the first and second fittings, each tongue being received in a groove and engaging a surface.

58. The connector assembly according to claim 42, wherein the first fitting includes a wall defining a bore and the stem member is axially slidable within the bore, wherein the stem member includes a plunger sealingly engaging the wall and wherein the connector assembly further comprises a seal positioned between the wall and the stem member.

59. The connector assembly according to claim 42, wherein the first fitting includes a sleeve defining a bore, the stem member includes a stem and a head mounted to the stem, and the head and the stem are axially slidable within the bore and wherein the ratchet mechanism is arranged between the sleeve of the first fitting and the stem of the stem member to resist retraction of the stem member from the second fitting.

60. The connector assembly according to claim 42, wherein the first fitting includes a first wall defining a first bore and a second wall defining a second smaller bore and the stem member includes a stem, a head mounted to one end of the stem, and a plunger mounted at the other end of the stem, wherein the plunger sealingly engages the first wall and is axially slidable within the first bore and the head and the stem are axially slidable within the second bore, and wherein the connector assembly further comprises a seal disposed between the stem member and the first wall.

61. The connector assembly according to claim 42, wherein the first fitting includes a first sleeve defining a first bore and a second sleeve defining a second smaller bore and the stem member includes a stem and a head mounted to one end of the stem, the head and the stem being axially slidable within the second bore and the ratchet mechanism being arranged between the stem and the second sleeve, and wherein the connector assembly further comprises a seal disposed between the piercing member and the first sleeve.

62. The connector assembly according to claim 42, wherein the first fitting includes a resilient mount positioned at the first aperture and wherein the first fitting, including the resilient mount, is integrally molded as a single part from a polymeric material.

63. The connector assembly according to claim 62, wherein the resilient mount includes a neck and a larger diameter hub mounted to the neck.

64. The connector assembly according to claim 62, further comprising at least one tongue extending between the first and second fittings to interlock the fittings, wherein the tongue and one of the first and second fittings are integrally molded as a single part from a polymeric material.

65. The connector assembly according to claim 42, wherein the second fitting includes a bore communicating with the second aperture and the stem member includes a head insertable into the bore, the head and the bore having mated tapered forms whereby the head can be frictionally engaged in the bore of the second fitting.

66. The connector assembly according to claim 65, wherein the second fitting further includes a larger counterbore communicating with the bore in the second fitting, the counterbore opening at the second aperture onto a seat and the second removable contamination containment layer contacting the seat.

* * * * *